United States Patent [19]

Chum et al.

[11] Patent Number: 4,942,269

[45] Date of Patent: Jul. 17, 1990

[54] PROCESS FOR FRACTIONATING FAST-PYROLYSIS OILS, AND PRODUCTS DERIVED THEREFROM

[75] Inventors: Helena L. Chum, Arvada; Stuart K. Black, Denver, both of Colo.

[73] Assignee: Midwest Research Institute, Kansas City, Mo.

[21] Appl. No.: 169,506

[22] Filed: Mar. 17, 1988

[51] Int. Cl.$^5$ .............................................. C07C 37/20
[52] U.S. Cl. ................................. 585/240; 568/762; 208/96; 528/1
[58] Field of Search ................. 568/762; 585/240; 528/1; 208/96, 263, 230, 204, 280

[56] References Cited

U.S. PATENT DOCUMENTS

| | | | |
|---|---|---|---|
| 2,172,415 | 9/1939 | Stewart | 204/9 |
| 2,203,217 | 6/1940 | Hund et al. | 260/627 |
| 3,069,354 | 12/1962 | Horingklee | 208/263 |
| 3,309,356 | 3/1967 | Esterer | 260/209 |
| 4,209,647 | 6/1980 | Gallivan et al. | 568/762 |
| 4,233,465 | 11/1980 | Gallivan et al. | 568/727 |
| 4,508,886 | 4/1985 | Russell et al. | 568/727 |

FOREIGN PATENT DOCUMENTS 38-16895 3/1963 Japan.

OTHER PUBLICATIONS

D. A. Nelson et al., Application of Direct Thermal Liquifaction for the Conversion of Cellulosic Biomass, Industrial Engineering Chemical Products Research Development, vol. 23, pp. 471–471 (1984).
H. Heineman, Hydrocaibons Pro Cellulose Waste, Petroleum refiner, pp. 161–163, vol. 23, No. 7, Jul. 1954.
H. L. Chum et al., Biomass Pyrolysis Oil Feedstocks for Phenolric Adhesives, ACS proceedings Symposium Adhesives from Reneuable Resources, Chapter 11, pp. 1∝2.
Behigni and I. S. Goldstein, Neutral Hydrolysis of Alkali Lignin to Monomeric Products, Jor. of Polymer Science: part C, No. 36, pp. 467–475 (1971).
L. Yur'ev et al., A Study of Equilibrium in the Extraction of Acid Components of Soluble Tar, Hydrolysis and Wood Chemistry, USSR, No. 3, pp. 17–19 (1976).
T. J. Elder and E. J. Solter, Pyrolysis of Lignocellulosic Materials, Phenolic Constituents of a Wood Pyrolytic Oil, Wood and Fiber, vol. 12 (4), pp. 217–222 (1980).
S. A. Nesmeyanov, Extraction of Phenols from Sewage Wastes by Phenosolvan, Chemical Abstracts, vol. 41, pp. 7595 (1951).
A. Dierichs, Removing Phenol from Industrial Waste Waters and Oils by the Phenosolvan Process, Chemical Abstracts, vol. 37, pp. 5532.
Erich Boye, The Phensolvan Process, Sewage and Wastes, vol. 24, pp. 2001 (1962).
A. Rieche and H. Seeboth, Removal of Phenols and Ammonia from Waters Diluted by Phenosolvan by (List continued on next page.)

Primary Examiner—Glenn Caldarola
Attorney, Agent, or Firm—Ken Richardson

[57] ABSTRACT

A process is disclosed for fractionating lignocellulosic materials fast-prolysis oils to produce phenol-containing compositions suitable for the manufacture of phenol-formaldehyde resins. The process includes admixing the oils with an organic solvent having at least a moderate solubility parameter and good hydrogen bonding capability, the solvent extracting the phenol and neutral fractions from the oils. The organic solvent-soluble fraction containing the phenol and neutral fractions is separated from the mixture and admixed with water to extract water-soluble materials therefrom. The organic solvent-soluble fraction is then separated from the water fraction and admixed with an aqueous alkali metal bicarbonate solution to extract strong organic acids and highly polar compounds from the solvent fractions. Finally, the residual organic solvent-soluble fraction is separated, and the organic solvent is removed therefrom to produce the phenol-containing compositions.

31 Claims, 2 Drawing Sheets

OTHER PUBLICATIONS

Means of Exchanger Resins, Sewage and Wastes, vol. 24, pp. 4541 (1962).

Ruldolf Bemmann, Removal of Oil from Phenosolvan Extracts, Chemical Abstracts, vol. 51, pp. 7696.

Kenneth H. Lanoutette, Treatment of Phenolic Wastes, Chemical Engineering/Deskbook Issue, pp. 99–106 (1977).

Kirk–Othmer, Encyclopedia of Chemical Technology, Third Edition, vol. 17, pp. 384–416 and Supplement vol., pp. 194–197.

J. D. Benigni and I. S. Goldstein, Neutral Hydrolysis of Alkali Lignin to Monomeric Phenols, Journal of Polymer Science: Part C, No. 36, pp. 467–475.

T. J. Elder and E. J. Soltes, Pyrolysis of Lignocellulosic Materials, Phenolic Constituents of a Wood Pyrolytic Oil, Wood and Fiber, vol. 12(4), pp. 217–226.

Kaj. G. Forss, Finnish Plywood, Particleboard, and Fiberboard Made with Lignin–Base Adhesive, Forest Products Journal, vol. 29, No. 7, pp. 39–43.

David A. Nelson et al., Application of Direct Thermal Liquefaction for the Conversion of Cellulosic Biomass, Industrial Engineering Chemical Products Research Development, vol. 23, pp. 471–475.

Jan Piskorz & Donald S. Scott, Lignin Derived Oils from the Fast Pyrolysis of Poplar Wood, Journal of Analytical and Applied Pyrolysis, vol. 12, pp. 51–59.

L. Yur'ev, et al., A Study of Equilibruim in the Extraction of Acid Components of Soluble Tar, Hydrolysis & Wood Chemistry, USSR, No. 3, pp. 17–19.

H. L. Chum et al., Biomass Pyrolysis Oil Feedstocks for Phenolic Adhesives, American Chemical Society Proc. of the Symposium: Adhesives from Renewal Resources, Chapt. 11, pp. 1–12.

PROCESS FOR FRACTIONATING FAST-PYROLYSIS OILS, AND PRODUCTS DERIVED THEREFROM

The United States Government has rights in this invention under Contract No. DE-AC02-83CH10093 between the United States Department of Energy and the Solar Energy Research Institute, a Division of the Midwest Research Institute.

BACKGROUND OF THE INVENTION

1. Field of the Invention

The present invention relates generally to the production of adhesive resins from biomass materials and, more particularly, to the treatment of fast-pyrolysis oils to make phenol-formaldehyde resins from lignocellulosic materials. Specifically, the present invention relates to a process for making phenol/neutral fractions suitable in the production of phenolformaldehyde resins from fast-pyrolysis oils derived from lignocellulosic materials.

2. Description of the Prior Art

Adhesive resins are utilized in a wide variety of applications including the bonding of wood layers to manufacture plywood (resoles), the formation of molded pieces and articles (novolaks), and the like. There are certain disadvantages, however, to existing techniques for the manufacture of phenolic resins. Phenol has been traditionally derived from petroleum-based products. Because the production of petroleum-based phenol can be quite expensive, there have been efforts in recent years to at least partially substitute the phenol in such resins with inexpensive phenols derived from wood-based products or extracts. More specifically, phenols derived from bark, wood chips and the like has been looked at as a potential substitute for petroleum-based phenol in such resins.

The pyrolysis of biomass, and in particular lignocellulosic materials, is known to produce a complex mixture of phenolic compounds which are derived primarily from the lignin fraction of the biomass. In nature, lignin acts as an adhesive to bind the cellulose fibers together. Therefore, lignin and lignin-derived material from wood seem like a natural starting point for the development of biomass-based adhesive resins. Sources for such phenolic materials include black liquor from kraft pulping and other pulping processes, where the lignin is present in a stream which is commonly burned to recover process heat and chemicals. Unfortunately, these lignins are generally not very reactive after recovery for a variety of reasons, such as high molecular weight, chemical modification during recovery due to condensation reactions and the like, and lack of reproducibility of proprieties. Various types of pyrolysis processes have also been utilized, frequently yielding similar kinds of results. Fast-pyrolysis, however, has proven to be an exception to this.

Fast-pyrolysis of biomass features the depolymerization of cellulosic, lignin, and hemicellulosic polymers which produces an oil having a relatively low molecular weight and which has considerable chemical activity under proper conditions. Crude pyrolysis oil apparently undergoes a limited amount of repolymerization upon physical condensation. However, the thermal stability of fast-pyrolysis oils at room temperature is qualitatively quite good implying a good shelf life for the oils, although at 100° C. the crude oils solidify overnight. Solidified pyrolysis oils are characterized by their low strength and brittleness. The potential of pyrolysis products for use in adhesive resins is not a new concept, as indicated above, but the efficient and cost-effective reduction of this to practice has been an elusive goal over many years.

The general approach of producing phenols from biomass has previously been to purify the phenolic fractions present in the pyrolysis oils by the use of solvents to partition the constituents by differences in solubility and reactivity. Different variations of solvents, reagents, and sequence of extractions have been developed in the past, and this has resulted in different partitioning coefficients for a couple of hundreds of chemical compounds known to be in pyrolysis oils, and therefore produced extracts having differing relative compositions. Another significant difference between various research efforts pertaining to this area in the past has been the type of pyrolysis used to produce the oils used as feed in the extraction process. These include updraft gasification, entrained fast-pyrolysis, and fluidized bed fast-pyrolysis, all at atmospheric pressures, as well as slow, high pressure liquefaction processes. In addition, both hardwoods and softwoods have been used as feedstock in the past for the oil forming processes. These differences in extraction and pyrolysis processes, coupled with the differences in feedstock, yield different materials as products. Thus, as indicated below, the usefulness of a particular extract as an adhesive component is quite different, one from the other.

U.S. Pat. No. 4,209,647 and No. 4,223,465 disclose methods for recovering phenolic fractions from oil obtained by pyrolysis of lignocellulosic materials and the subsequent use of that fraction in making of phenol-formaldehyde resins. However, these processes use pyrolysis oils which are usually formed at ill-defined temperatures and which have undergone phase separation cracking and some condensation, and suffer from very low yields.

A number of other patents including U.S. Pat. No. 2,172,415, No. 2,203,217, No. 3,069,354, No. 3,309,356 and No. 4,508,886 as well as Japanese Patent No. 38-16895 all disclose a variety of processes for recovering phenolic fractions from oils derived from biomass materials and oil resources. These processes vary in the particular procedures and techniques utilized to ultimately separate the phenolic fractions as well as the procedures utilized to derive the oil from the biomass or other feed material. However, they all have a common thread linking them in that the ultimate end product is a phenolic fraction, which is desired to be as pure as possible. This phenolic fraction is then utilized to produce phenol-formaldehyde resins. The phenol substitutes usually were slower than phenol derived from petroleum-based products. The complex procedures disclosed in there references to produce relatively pure phenolic fractions are not particularly economical. Thus, there is still a need for a process designed to produce pyrolysis oils from lignocellulosic materials and then extract a phenolic composition from such oils which is capable of functioning as efficiently as petroleum-based phenols in the formation of phenol-formaldehyde resins and which is less expensive to produce.

SUMMARY OF THE INVENTION

Accordingly, it is one object of the present invention to provide a process of producing a phenol-containing composition from biomass material.

It is another object of the present invention to provide an improved and simplified process of fractionating fast-pyrolysis oils derived from lignocellulosic materials.

Another object of the present invention is to provide an inexpensive phenolic composition suitable for use in the production of adhesive resins.

Yet another object of the present invention is to provide a process of producing a composition containing phenol and neutral fractions from fast-pyrolysis oils.

To achieve the foregoing and other objects and in accordance with the purpose of the present invention, as embodied and broadly described herein, a process is disclosed for fractionating fast-pyrolysis oils to produce phenol-containing compositions suitable for manufacturing phenol-formaldehyde resins. The process includes admixing the oils with an organic solvent having at least a moderate solubility parameter and good hydrogen bonding capability, the solvent extracting the phenol and neutral fractions from the oils. The organic solvent-soluble fraction containing the phenol and neutral fractions is separated from the mixture and admixed with water to extract water-soluble materials therefrom. The organic solvent-soluble fraction is then separated from the water fraction and admixed with an aqueous alkali metals bicarbonate solution to extract strong organic acids and highly polar compounds from the solvent fraction. Finally, the residual organic solvent-soluble fraction is separated, and the organic solvent is removed therefrom to produce phenol-containing compositions.

BRIEF DESCRIPTION OF THE DRAWINGS

The accompanying drawings which are incorporated in and form a part of the specification illustrate preferred embodiments of the present invention, and together with the description, serve to explain the principals of the invention. In the drawings.

DETAILED DESCRIPTION OF THE PREFERRED EMBODIMENTS

Figure 1:
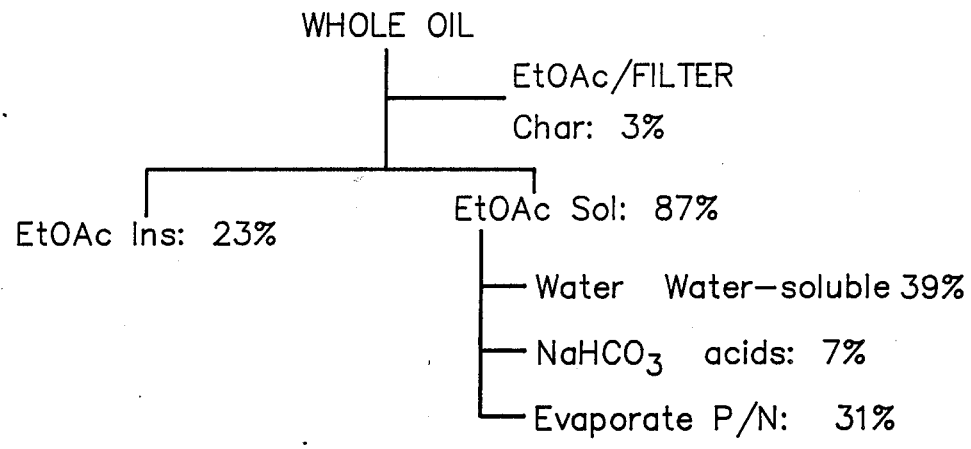
FIG. 1 is a flow diagram illustrating the process of the present invention.

During the course of studying the problem of producing inexpensive but effective phenolic compositions from biomass, it was discovered that certain polar organic solvents having at least a moderate solubility parameter, moderate degree of polarity, and good hydrogen bonding capabilities were capable of extracting both phenol and neutral fractions from fast-pyrolysis oils. Moreover, it was discovered that this extraction technique was equally effective for fast-pyrolysis oils of differing starting materials. Thus, it was discovered that the present invention may be utilized with pyrolysis oils derived from pine sawdust, bark, grasses, softwoods as well as certain hardwoods with very little differences in the final results. Apparently, the fast-pyrolysis process preserves the delicate products in monomeric and oligomeric states. A key factor in the process of the present invention is that the oils derived from the lignocellulosic materials must be done so utilizing a fast-pyrolysis. Fast-pyrolysis is generally known in the art, and such a technique has been specifically disclosed in an article entitled, "Production of Primary Pyrolysis Oils in a Vortex Reaction", American Chemical Society Division of Fuel Chemistry Preprints, Vol. 32, No. 2, pp. 21-28 (1987). Thus, details of such fast-pyrolysis techniques need not be specifically repeated and disclosed herein, and the contents of this Article are therefore specifically incorporated herein by reference. Oils from other fast-pyrolysis concepts are also good feedstocks. Such concepts are referenced in "Fast-Pyrolysis of Pretreated Wood and Cellulose", Ibidem, pp. 29-35 (1987), "Preliminary Data for Scale up of a Biomass Vacuum Pyrolysis Reactor", Ibidem, pp. 12-20 (1987); "The Role of Temperature in the Fast-Pyrolysis of Cellulose and Wood", Industrial Engineering Chemistry Research, Vol. 27, pp. 8-15 (1988), and "Oil From Biomass by Entrained Flow Pyrolysis", Biotechnology and Bioengineering Symposium, No. 14, pp. 15-20 (1984).

In general, the biomass solids in such fast-pyrolysis of biomass solids entrain the feedstock particulates tangentially at high velocities into a vortex reactor tube which has an internal surface design that guides the centrifuged solids into a tight helical pathway on the reactor wall. This results in a very high heat transfer to the wood or other feedstock particles which allows mild cleavage of the polymeric components of the feedstock. Consequently, high yields (greater than 55%) of dry woods and bark oils are generally obtained. If the feedstock is not fully pyrolyzed, the solids enter a recycle loop located at the end of the vortex reactor. After attrition to a powder, char particles elute with the vapor stream and are isolated in a char cyclone. Alternative methods to produce primary pyrolysis oils thought to be similar to fast-pyrolysis include fast-pyrolysis in fluidized beds and in entrained flow reactors.

Utilizing the process of the present invention, the pyrolysis oils are fractionated in a unique way which produces a combined phenolics and neutral fraction of high phenolic hydroxyl and aldehyde content. In general, a polar organic solvent is added to the oils to separate the phenol and neutral fractions from said oils. The organic solvent-soluble fraction is then admixed with water to extract water-soluble materials, and then further washed with an aqueous alkali metal bicarbonate solution to extract strong organic acids and highly polar compounds. The residual organic solvent-soluble fraction containing the phenol and neutral fractions is then isolated, and the organic solvent is removed, preferably by evaporation, to produce a phenol-containing composition having the phenol and neutral fractions of the original raw oils. The yield of the phenolics and neutrals fraction in the extract is about 30% of the fast-pyrolysis oil derived from sawdust and about 50% of the oil derived from bark.

In prior art phenol-producing processes, the processes ended only after the phenolic-containing compositions were generally reduced to purified phenolics only, with the neutral fractions also be removed. By neutral fractions, it is meant those compounds which are not solubilized by a strong base such as sodium hydroxide, and have molecular weights of approximately 100–800. Such neutral fractions include carbonyl compounds, furfural-type compounds and the like. It was apparently previously believed that such neutral fractions must also be extracted in order to provide a phenol composition which may be utilized as a substitute for petroleum based phenols in the production of phenol-formaldehyde adhesive resins. It has been discovered, however, that by utilizing the process of the present invention, the resultant composition containing both phenol and neutral fractions function just as well as and in some aspects better than relatively pure phenol composition in the production of phenol-formaldehyde resins because since the compositions have aldehyde groups, much less formaldehyde is needed to make these formulations. Reduced formaldehyde levels lead to minimization of potential environmental problems. In addition, the economics are such that it is substantially less expensive to manufacture the combined phenol and neutral fraction composition. Moreover, by utilizing the entire fraction which includes phenolic compounds and neutral compounds as feedstocks for resins, we discovered that this prevented the pyrolysis-derived reactive phenolics from undergoing air oxidation under alkaline conditions, which is what prevails when one isolates and purifies the phenolics fraction alone. This latter air oxidation which can be a problem is a type of condition that prevails in many prior art techniques and is accomplished by extractions with aqueous sodium hydroxide solutions, and accompanied by the formation of insoluble tars and reduced yields of phenolics.

Investigations of the fractionation scheme of the present invention as generally described above utilizing pine fast-pyrolysis oils were carried out employing a number of different solvents to determine the preferred and optimum solvents and the requirements thereof. In general, the whole oil was first dissolved in the organic solvent preferably in an oil:solvent ratio of 0.5:1 to 1:3 by weight. The oil was initially filtered to separate char which is carried over from the pyrolysis reactor operations. Upon standing, the solvent/oil mixture then separates into two phases, the solvent-soluble phase and the solvent-insoluble phase.

One requirement for the organic solvent is that the solvent and water exhibit low mutual solubility. Preferably, acceptable solvents include those with solubilities that are not more than about 10 grams of solvent in 100 grams of water and about 3 grams of water in 100 grams of solvent, in terms of mutual solubility. Thus, this solvent requirement eliminates all low-molecular-weight alcohols (methanol, ethanol, propanol) that are infinitely soluble in water, methylethylketone, the carboxylic acids (formic, acetic and propionic) which are infinitely soluble in water, and methyl formate. The classes of solvents that would be acceptable only from a pure mutual solubility point of view include hydrocarbons (aliphatic, aromatic), higher alcohols (greater than 6 carbon atoms), higher ketones (greater than 5 carbon atoms), esters (greater than 2 carbon atoms), ethers, polychlorinated hydrocarbons, and higher nitriles (greater than 4 carbon atoms).

Another requirement for the organic solvent which further limits potential candidates is that the solvent have a low boiling point or a low-boiling point azeotrope. The preferred boiling point is around 100° C., although this is somewhat relative. Yet another requirement for the organic solvent is that the solvent have some degree of polarity, preferably high polarity, as well as high hydrogen bonding capability in addition to a moderate-to-good solubility parameter. The solubility parameter is defined as a measure of all the intermolecular forces present in the solvent. The overall solubility parameter is composed of components due to dispersive forces, polar forces (caused by a high dipole moment in the molecule), and hydrogen bonding capability. Solubility parameters, measured in $[cal/cm^3]^{\frac{1}{2}}$, range from 5–7 for hydrocarbons and non-polar solvents, to 14.5 for methanol and 23.4 for water-highly polar substances. Thus, low boiling point ethers, such as diethyl ether, are excluded from being preferred solvents since they have a very low solubility parameters (7.4) and very low polar components (1.4). Hydrocarbons are also excluded as preferred solvents because of their very low polar components and overall low solubility parameters.

It has been found that the preferred group of solvents for use in the present invention include acetate and propionate esters, methyl alkyl ketones and ethyl alkyl ketones. More specific preferred organic solvents are listed below in Table I, the most preferred being ethyl acetate due to its availability, relatively low solubility in water, and high oil solubility. The most preferred range for solubility parameters includes 8.4–9.1 with polar components in the 1.8–3.0 range and hydrogen bonding components in the 2–4.5 range. Additional acceptable solvents are the isomers of those listed in Table I. Mixtures of esters are also acceptable as are mixtures of the higher ketones. Ternary solvent systems also are possible, primarily mixtures of esters and high molecular weight ethers such as diisopropylether to reduce the boiling point. However, the most preferred solvents for use with the present invention are ethyl acetate, as indicated above, as well as butyl acetate and methylisobutylketone.

TABLE I

| Property | Acetate Esters | | | Methyl Ketones | | | Ethyl Ketone |
|---|---|---|---|---|---|---|---|
| | Ethyl | Propyl | Butyl | i-Butyl | i-Amyl | i-Propyl | Ethyl |
| Mol. wt | 88.1 | 102.1 | 116.2 | 100.2 | 114.2 | 86.14 | 86.14 |
| Boiling Point, °C. (at 70 mm Hg) | 77.1 | 101.5 | 126.1 | 116.5 | 144 | 92 | 102.0 |
| Density, 20° C. | 0.90 | 0.89 | 0.88 | 0.80 | 0.88 | 0.81 | 0.81 |
| Heat Vaporization, | | | | | | | |
| kcal/mole (20° C.) | 8.4 | 9.3 | 10.4 | 10.00 | | | |
| kcal/mole (b.p.) | 7.71 | 8.20 | 8.58 | 8.50 | | 7.73 | 8.06 |
| Solubility, wt % in water | 8.08 | 2.3 | 0.43 | 1.7 | ~0 | ~2 | 2.4 |
| Water in Azeotrope | 2.94 | 3.9 | 1.86 | 1.9 | ~0 | ~2 | 2.6 |
| Water wt % | 9.47 | 14 | 28.7 | 24.3 | 44.0 | | 24 |
| boiling point, °C. | 70.38 | 82.2 | 90.2 | 87.9 | 94.7 | | 82.9 |

TABLE I-continued

| Property | Acetate Esters | | | Methyl Ketones | | | Ethyl Ketone |
|---|---|---|---|---|---|---|---|
| | Ethyl | Propyl | Butyl | i-Butyl | i-Amyl | i-Propyl | Ethyl |
| Dielectric Constant | 6.02 | 6.00 | 5.01 | 13.11 | | | 17.0 |
| Solubility param. Total | 9.1 | 8.4 | 8.46 | 8.57 | 8.55 | 8.5 | 8.8 |
| Dispersive comp. | 7.44 | 6.6 | 7.67 | 7.49 | 7.80 | | ~7.8 |
| Polar comp. | 2.6 | 2.0 | 1.8 | 3.0 | 2.8 | | ~3.4 |
| H-Bonding comp. | 4.5 | 4.8 | 3.1 | 2.0 | 2.0 | | 2.0 |

As indicated above, the preferred solvent is ethyl acetate, and the process of the present invention will hereinafter be described in terms of utilizing ethyl acetate as the solvent. However, it should be understood that any of the identified solvents may be utilized in the following described process. As previously indicated the whole oil is dissolved in the ethyl acetate at a preferred pH of about 2-4 and then filtered. Upon standing, the ethyl acetate/pyrolysis oils mixture separates into two phases. Chemical spectroscopic analysis revealed that the ethyl acetate-insoluble fraction contains carbohydrate and carbohydrate-derived products. The ethyl acetate-soluble fraction, containing the phenol/neutral fractions, is then separated and washed with water to remove the remaining water-soluble carbohydrate and carbohydrate-derived materials, preferably in a 1:6 to 1:1, water:oil weight ratio. The ethyl acetate-soluble fraction is then further extracted with an aqueous metal bicarbonate solution, preferably an aqueous sodium bicarbonate solution, 5% by weight. The pH of the bicarbonate extraction solution is preferably maintained at approximately 8-9.5, and a 6:1 to 0.5:1 bicarbonate solution:oil weight ratio is preferably utilized. The aqueous bicarbonate layer extracts the strong organic acids and highly polar compounds, and the remaining ethyl acetate-soluble layer contains the phenols and neutral fractions. This ethyl acetate-soluble layer is then separated, and the ethyl acetate solvent is evaporated using any known evaporation technique, including vacuum evaporation techniques. The dried phenol/neutral fraction typically contains 0.5-1% of water with traces of ethyl acetate. Table II illustrates typical yields for various pine sawdust fast-pyrolysis oils and fractions of oils obtained during different test runs as well as for Douglas fir bark fast-pyrolysis oils.

TABLE II

Yields for Various Pyrolysis Oils

Wt % Yields of Pyrolysis Oils Based on Dry, Char-Free Oil

| Pyrolysis Oil | EtOAc Insol | Water Sol. | Organic Acids | Phenol/Neut. | |
|---|---|---|---|---|---|
| Pine sawdust | 42.8 | 24.7 | 5.7 | 21.3[a] | |
| Pine sawdust | 28.2 | 39[c] | 6.1 | 26.7[b] | |
| Combined pine oil[d] | 22.8 | 28.9 | 6.7 | 25 | |
| Pine sawdust | 41[e] | 27.2 | 6.3 | 26 | |
| Douglas fir bark | 0 | 12.1 | 15 Solids:2.9 | Phenols: 47.8 | Neutrals: 15.6 |
| Douglas fir bark | 0 | ND* | 19 Solids:4.8 | Phenols: 50.8 | Neutrals: 17 |

[a] Phenolics: 16.5; Neutrals: 9.5
[b] Phenolics: 16.5; Neutrals: 6.0
[c] Water solubles by difference
[d] From two condensers
[e] EtOAc insolubles by difference
*Not Determined As indicated in Table II, the aqueous alkali metal bicarbonate solution utilized to extract strong organic acids and highly polar compounds further purifies the phenol/neutral fractions. While any suitable alkali metal bicarbonate solution may be utilized, the preferred solution is selected from sodium bicarbonate, potassium bicarbonate, lithium bicarbonate and ammonium bicarbonate, with sodium bicarbonate being the preferred and most optimal solution. From the aqueous bicarbonate solution, it is possible to isolate a fraction rich in organic acids as a by-product. In this instance, the aqueous layer can be neutralized, for example with 50% by weight of phosphoric acid (although other acids can be used) saturated with sodium chloride, and extracted with ethyl acetate. It is possible to then evaporate the solvents and isolate the remaining fractions as well.

The phenols/neutrals fraction can be further fractionated into isolated phenolics and neutrals if desired. This can be accomplished by utilizing a 5% by weight solution of sodium hydroxide in a volume ratio of 5:1 of solution:extract. The aqueous layer is then acidified to a pH of about 2 utilizing a 50% solution of phosphoric acid (although other acids can be used). It is then saturated with sodium chloride and extracted with ethyl acetate. Evaporation of the solvent leads to the isolation of the phenolics fraction; evaporation of the initial ethyl acetate solution freed from phenolics leads to the neutrals fraction. It should be noted, however, that the present invention does not require this separation of the phenol from the neutral fractions, and it is in fact this aspect of the present invention which makes the present process so economic. In the past, as previously indicated, the phenolics have always been the desired end-product, and sodium hydroxide has typically been utilized in such process treatment. This is unnecessary with the process of the present invention, for it has been discovered that the combined phenolic and neutral fraction composition is sufficiently pure to function by itself in the formation of adhesive resins.

The process of the present invention can be operated in both batch mode as well as in a continuous mode. In the batch mode embodiment, the whole oils are extracted with ethyl acetate and then washed with water. Following the water wash, the composition is then washed with the aqueous sodium bicarbonate to eliminate the acidic components, which come from pyrolysis of the carbohydrate fraction and would be deleterious to the resins. In a continuous operation, the pyrolysis oil is preferably extracted simultaneously with water and ethyl acetate, and then the ethyl acetate's soluble fraction is extracted countercurrently with the aqueous bicarbonate solution. The whole ethyl acetate fraction, which includes both phenolic and neutrals compounds, is then utilized as a feedstock for resins after solvent evaporation.

EXAMPLE I 1.0 kg of fast-pyrolysis oil derived from pine sawdust was dissolved into 1 kg of ethyl acetate. After filtration of the solution, this solution then separated into two easily identified and separated phases. The ethyl acetate-soluble phase was then isolated, and 0.8 kg of water was added to this phase. The resulting water-soluble fraction was isolated and saved for further processing. 2 kg of 5% sodium bicarbonate solution was then added to the ethyl acetate-soluble fraction, and the aqueous phase therefrom was saved for further processing. This aqueous phase was the acids-soluble fraction. The resulting washed ethyl acetate-soluble solution, containing the phenol and neutral fractions, was then solvent evaporated to remove the ethyl acetate solvent. The yield of phenol/neutral was 31% by weight based on the dry oil.

The remaining ethyl acetate-insoluble fraction was solvent evaporated and yielded 23 weight percent of the starting dry oil. The aqueous wash yield after solvent evaporation was 39 weight percent of the oil. The aqueous bicarbonate solution was neutralized with a 50% phosphoric acid solution, and after saturation with sodium chloride, the organic phase was extracted into ethyl acetate. After solvent evaporation, the acids fraction yield was approximately 7 weight percent. FIG. 1 illustrates this mass balance of the various fractions resulting from this Example I utilizing the process of the invention.

EXAMPLE II 9.5 kg of fast-pyrolysis oils derived from pine sawdust were dissolved into 10 kg of ethyl acetate. After filtration, this solution settled into two easily identified and separated phases. 1.8 kg of water was then added to the ethyl acetate-soluble phase, and this solution was then separated into two easily identified and separated phases. The resulting water-soluble fraction was saved for further processing, and the other ethyl acetate-soluble fraction was then admixed with 8.9 kg of a 5% sodium bicarbonate solution. The aqueous phase of this solution was then separated and saved for further processing, which was the acids-soluble fraction. The resulting washed ethyl acetate-soluble solution, containing the phenol/neutral fraction, was separated, and the solvent was then evaporated. The yield of the phenol/neutral fraction was 30% by weight based on dry oil.

Using a procedure similar to that described above in Example I, the mass balance of the fractionation was determined as follows: the ethyl acetate insoluble fraction comprise 21 weigjht percent, the water-soluble fraction comprise 31 weight percent, and the organic acids comprise 7.2 weight percent.

EXAMPLE III

The fractionation of Douglas fir pyrolysis products which are solids at room temperature, was similar to that described for pine. 4.6 kg of Douglas fir fast-pyrolysis product were dissolved into 9.8 kg of ethyl acetate solution. No ethyl acetate insoluble fraction was observed. The whole solution was then extracted with 12 kg of a 5 weight percent aqueous sodium bicarbonate solution. The ethyl acetate-soluble solution contained 68 weight percent of phenolics and neutrals. The phenols and neutrals were then separated by extraction with 11 kg of a 5 weight percent aqueous solution of sodium hydroxide. From the ethyl acetate solution, 17 weight percent of neutrals were obtained. The alkaline aqueous solution, containing the phenolics, was acidified with 50% phosphoric acid, although other acids could have been used. This solution was then saturated with sodium chloride and extracted with ethyl acetate to yield 50.8 weight percent for the phenolics fraction upon solvent evaporation. In the extraction with aqueous bicarbonate solution, a precipitate was formed (5 weight percent) along with the soluble acids fraction of 19 weight percent. The data for the fractionated materials are provided in Table II above.

EXAMPLE IV

Fast-pyrolysis oil derived from pine sawdust was also fractionated on a continuous basis. The continuous process utilized, but is not limited to, a 6-stage system of mixer tanks and settling tanks. The oil, ethyl acetate, and water were mixed and allowed to settle with the organic phase being sent on to multi-stage extraction with 5 weight percent aqueous sodium bicarbonate solution with each extraction stage having a separate settler tank. The bicarbonate extraction was run countercurrent to the flow of the organic phase. The aqueous fractions, that is the combined ethyl acetate insoluble and water-soluble fractions, the aqueous bicarbonate solution, and the organic phase were all collected and processed as described above. Conditions of the extraction included the following: oil flow, water flow, ethyl acetate flow, and aqueous bicarbonate flow rates were 10, 6, 34, and 35 mL/min, respectively. It should be noted, however, that the countercurrent continuous extraction process is not limited to these flow rates. The yield of phenol/neutral fraction composition was about 20% based on the oil flow rate and phenol/neutral isolated fractions. A total of 20 kg of oil was fractionated in this way. Variations in flow rates and number of settler and mixer tanks, however, can yield different proportions of materials. Phase separation was readily accomplished within the settlers.

Analysis of the products from intermediate stages of extraction revealed that 1–3 stages of bicarbonate extraction may be used. Turning from the Examples given above, the fractionation scheme described above allowed the isolation of 21% to 31% of the starting pine oils as a phenol/neutral fraction, or overall yields of 12–21% based on starting dry wood. This fraction consisted of approximately 73% phenolics, extractable from sodium hydroxide solution from an ethyl acetate solution, and 27% neutrals. The total yield of phenol/neutral fraction isolation is reproducible as shown by the runs in Table II above.

The typical oil contained 6.2% phenolic hydroxyl and 0.4% carboxylic acid contents by weight ranges. Ranges of 5.5–6.5% phenolic hydroxyl and 0.1–0.6% carboxylic acid contents are expected for the different starting feedstocks. The phenol/neutral fraction included about 6.6% phenolic hydroxyl content and no carboxylic acid content. Expected ranges for phenols/neutrals are 6.0–12% depending on the feed. The acids fraction included about 9.2% phenolics and 0.9% carboxylic acid contents. Ranges for various feedstocks are 5–10% for phenolics and 0.5–3% carboxylic acid contents.

In characterizing the resultant phenol compositions, the apparent molecular weight distributions obtained from gel permeation chromatography on polystyrene-divinylbenzene copolymer gels (50 Angstrom) with tetrahydrofuran as solvent, indicated that the phenolics fraction had components ranging from the monomeric substituted phenols (around 150) to oligomers (up to several thousand in molecular weight). The acids and neutrals had the lowest molecular weight components. From molecular beam mass spectra of the phenol/neutral fractions, a number of phenolic compounds were detected: guaiacol (2-methoxyphenol) m/z 124; catechols m/z 110; isomers of substituted 2-methoxyphenols with alkyl groups such as methyl (m/z 138), vinyl (m/z 150), 3-hydroxy-propen(1)-yl (m/z 180), allyl (m/z 164), hydroxyethyl (m/z 168), and ethyl (m/z 152), most likely in the p-position. In addition, carbohydrate-derived compounds were present such as furfural alcohol and a number of other furfural derivatives.

From proton nuclear magnetic resonance spectrum of the phenol/neutral fraction, of the total intensity, the aromatic protons (6.5–10 ppm) constituted 52%, the aliphatic (1.5–3.5 ppm) about 20%, and the methoxy region and oxygenated and side-chain region (3.0–4.2 ppm) constituted 30%. This was in agreement with the description from the molecular beam mass spectra of mixtures of phenolics with substituted groups. The carbon-13 nuclear magnetic resonance spectra confirmed this data.

Bark derived phenols have a very high phenolic hydroxy content (7.4–11.5%) depending on pyrolysis conditions (steam to nitrogen carrier gas) and therefore are very suitable for adhesive formulation replacing phenol at greater than a 50% level.

As previously indicated, a principal purpose of producing the phenol/neutral fraction is to provide a substitute for pure phenol in the production of resins and the like. Specifically, novolaks, which are phenol-formaldehyde resins made under acidic conditions, and resoles, which are phenol-formaldehyde resins formed under alkaline conditions for gluing to plywood, were produced and compared to novolaks and resoles utilizing standard formulations of commercially available phenol. Specifically, phenol at a pH of 11 with twice the molar amount of formaldehyde was compared with Cascophen 313, a commercial softwood plywood resin by Borden Chemicals. At 124° C., Cascophen 313 took 12.2 min to gel, whereas the phenol with added paraformaldehyde did not gel even after 30 min.

Of the various fractions of pyrolysis oil, only the phenol/neutral fraction gave a positive gel test under the above conditions. In preliminary gel testing of the phenol/neutral extract, one gram of paraformaldehyde was arbitrarily added to 4 grams of the extract. The pH of the extract was adjusted by adding 0.2–0.1 mL of 50% by weight sodium hydroxide. There appeared to be a strong buffering of the pH by the extract at a pH 9.5. Cascophen 313 was used for comparison. At 0.5 mL of added sodium hydroxide, the gel time of the phenol/neutral fraction was much shorter than that of the Cascophen, with a gel time of only 29% that of Cascophen at 124° C. At 112° C., it was 34%, while at 101° C. it was 46% of Cascophen. At the original pH of 3 of the phenol/neutral fraction, there was no gelling of the mixture even at 132° C. with the same amount of added paraformaldehyde.

Test novolak samples were then prepared and were characterized by solid-state carbon-13 cross polarization/magic angle spinning nuclear magnetic resonance (CP/MAS NMR) spectra as well as solution NMR. The spectra of a phenol-formaldehyde novolak were compared with thereof a similar novolak in which 50% by volume of the phenol was replaced with the phenol/neutral fraction from fast-pyrolysis of pine sawdust in accordance with the present invention. The authentic novolak produced main peaks (from deconvolution) at 150, 130 and 120 ppm corresponding to hydroxysubstituted aromatic carbons, unsubstituted meta-aromatic carbons, and unsubstituted para-aromatic carbons, respectively. In the aliphatic region, the main peaks were at 35 and 40 ppm, assigned to ortho-para methylene bridges and para-para methylene bridges, respectively. The presence and intensity of such peaks corresponded to the formation of random novolaks. On substitution of phenol with the phenol/neutral fraction produced in accordance with the present invention, the key peaks of the random novolak remained, but peaks characteristic of the types of phenolic compounds present also appeared such as at 150 ppm (meta-aromatic carbons attached to methoxy groups), 55 ppm (methoxy groups), and 20 ppm aliphatic groups.

Key differences between the authentic novolak and the phenol/neutral-substituted novolak produced from the process of the present invention were in relative peak intensities. While the ratio of unsubstituted meta-aromatic carbons to ortho-para methylene bridges (130 to 35 ppm) in the authentic sample was roughly 7:1, the ratio in the phenol/neutral novolak was approximately 4:1 (60% of the original value). Such a difference was anticipated, since the phenol/neutral novolak of the present invention contained a number of meta-substituted methoxy compounds. The phenolformaldehyde novolak had a high ratio of hydroxy-substituted aromatic carbons (150 ppm) to unsubstituted meta-aromatic carbons (130 ppm) than the phenol/novolak of the present invention (40% vs 30%). Molding compounds have been made with the novolaks developed with 50% replacement of phenol with phenols/neutrals that had identical tensile and flexural strength and just slightly lower Izod impact resistance. This latter parameter is controlled by the type filler used and can be improved.

Figure 2:
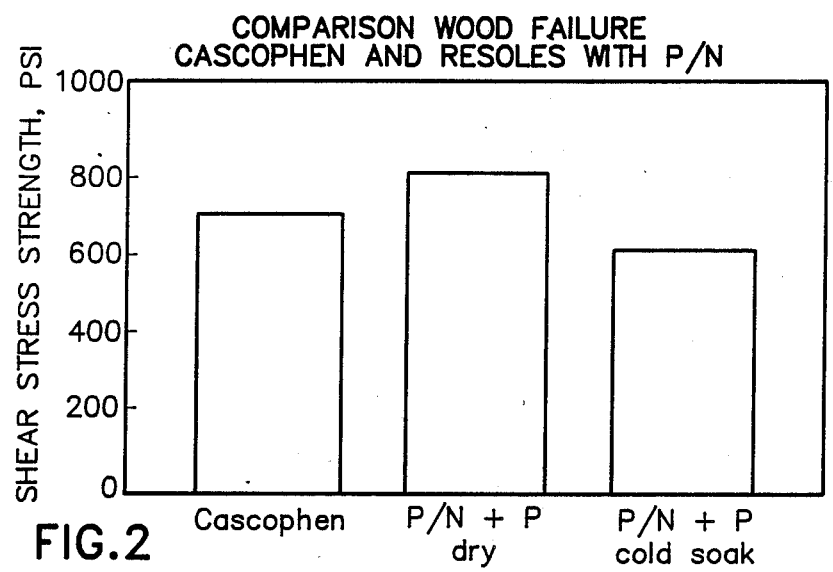
FIG. 2 is a graph illustrating sheer stress strength of resin adhesives produced from the end-products of the present invention compared to a commercial product.

A few preliminary resoles have also been made utilizing a 50% replacement of phenol with the phenol/neutral fraction produced by the process of the present invention. FIG. 2 discloses a comparison of stress shear strength between Cascophen and resoles produced with phenol/neutral fractions of the present invention. Specimens were tested after a cold water soak (rightmost bar) and met test requirements. As can be seen from FIG. 2, the Cascophen showed a shear stress strength in psi of approximately 700, while the resole with the phenol/neutral fraction produced from the present invention showed a strength of approximately 800 psi, significantly higher than Cascophen. Moreover, the resole produced from the phenol/neutral fraction of the present invention illustrated a cold soak strength of approximately 600, which is considerably higher than the standard of 500 which has generally been set for existing products such as the Cascophen. The tests performed used the British standard 1204; Part 1: 1964, and the testing of 10 specimens per evaluation. Thus, FIG. 2 illustrates the fact that the shear strength of resins produced by substituting 50% of the phenols therein with the phenol/neutral fraction produced with present invention are in fact stronger than phenolformaldehyde resins utilizing pure phenol.

Figure 3:
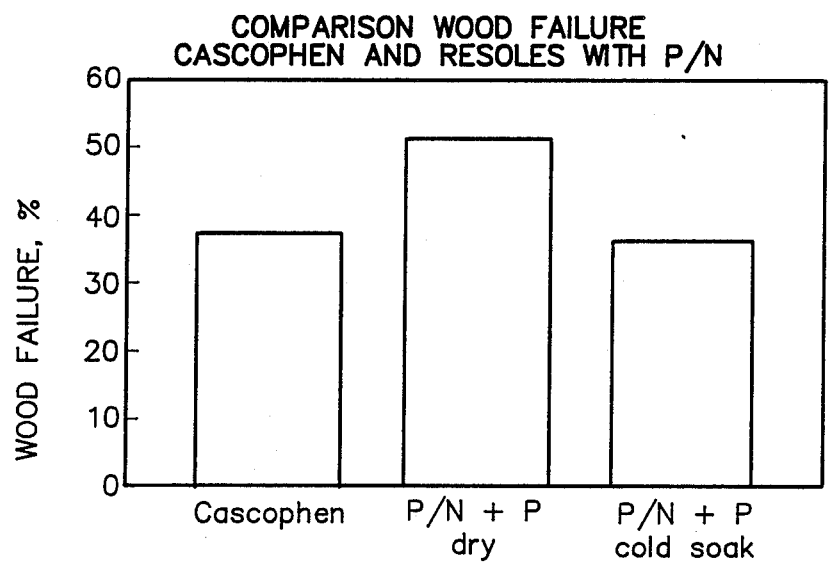
FIG. 3 is another graph illustrating wood failure test results of the adhesive resins produced from the end products of the process of the present invention compared to a commercial adhesive product.

Referring to FIG. 3, wood failure tests are compared between the Cascophen and resoles having the phenol/neutral fraction produced from the present invention. To interpret FIG. 3, it should be understood that it is preferred to have a wood failure, not a resin failure. Thus, if the wood fails, the resin is deemed to be good, and if the resin fails, it is deemed not to be good since the resin has actually separated. Thus, it is desirable to have a higher wood failure percent in order to show resin strength. Referring to FIG. 3, it should be clear that the Cascophen samples had a wood failure of approximately 38%, while the resin produced by substituting 50% of the phenolic portion with the phenol/neutral fraction from pyrolysis oils was well over 50%, illustrating a significant difference in resin strength capability. Moreover, the cold soak test results illustrated that the resole having the phenol/neutral fraction produced from the present invention had a cold soak rating the same as a non-cold soak rating of the Cascophen. Thus, these tests further indicated that resole resins produced by substituting 50% of the phenol with the phenol/neutral fraction produced from the present invention are considerably better in function and strength than standard commercially available products. The tests performed used the British standard 1204: Part 1: 1964, and testing of 10 specimens per evaluation.

With respect to the economic benefits of the present invention, petroleum derived phenol costs about $0.34 (spot price) and $0.40 (list price) per pound. Prior to the present invention, the main competition has been the lignin-derived substitutes from commercial pulping processes. Kraft lignins have to made chemically more reactive to replace phenol in phenol-formaldehyde resins with similar performance. These commercial products are sold as resin co-reactants, and their price ranges from $0.33–$0.85 per pound depending on the reactivity needed (based on kraft lignins). Less expensive products are available as fillers in the $0.19 per pound range. The materials derived from the process of the present invention are co-reactants with the ability to replace about 50% of the phenol in phenol-formaldehyde resins as described above. Indications are that for molding compounds and for plywood adhesive resins, 50% phenol replacement would provide a very similar performance to the commercial phenolic adhesives, and in fact would give a better performance as illustrated and described above in FIGS. 2 and 3. However, there is a significant cost reduction factor in that the phenol-formaldehyde fractions produced from the phenol/neutral composition of the present invention have an amortized cost projected at approximately $0.16 per pound compared to $0.34–$0.40 per pound for commercial phenol. If the lignocellulosic starting material is bark, this cost is even less because the yield of phenolics from the bark is higher than that of sawdust or pine. Plant sizes were 250 to 1000 tons of feedstock per day, 15% return on capital, plant life of 20 years, and waste sawdust at $10.00 per dry ton.

As described above, the most developed application for the end-products of the present invention is the replacement of 50% and potentially more of phenol in phenol-formaldehyde resins for use as molding compounds, foundry, and shell moldings. Other potential applications for the resulting product of the process of the present invention include the replacement of phenol in softwood and hardwood plywood resins, the insulation market, composite board adhesives, laminated beams, flooring and decking, industrial particle board, wet-formed hard boards, wet-formed insulation boards, structural panel board, and paper overlays. Alternative adhesive systems from the carbohydrate-rich fractions of the present invention could also be made.

In addition, another product that can be derived from the other fractions of the pyrolysis oils is an aromatic gasoline. Passage of vapors of these compounds over zeolite catalysts produces high octane gasoline, as more clearly discussed in "Low-pressure upgrading of Primary Pyrolysis Oils form Biomass and Organic Waste", in Energy from Biomass and Wastes, Elsevier Applied Science Publishers, London, pp. 801–830 (1986).

A final advantage to the present invention is that about one-third of the usual amount of formaldehyde employed in conventional phenolic adhesives is necessary in producing adhesives wherein 50% of the phenol is substituted with phenol/neutral fractions provided by the present invention. Since there is significant environmental concern over formaldehyde emissions from resins, the products resulting from the process of the present invention therefore become very important from this context.

As can be seen from the above, a novel process for fractionating fast-pyrolysis oils to produce phenol-containing compositions having phenol/neutral fractions contained therein suitable for manufacturing phenol-formaldehyde resins are disclosed. The process is simple and economic, and can be used in either batch or continuous mode operations. The resulting phenol-neutral composition can be subsequently utilized to produce novolaks and resole resins of comparable or superior performance characteristics relative to standard phenol-formaldehyde resins yet the pyrolysis-derived phenolic feedstocks are projected to cost less than half of the cost of petroleum-derived phenol. Moreover, these resulting resins have numerous different types of applications, and the cost benefits alone are significant.

While the foregoing description and illustration of the present invention has been particularly shown in detail with reference to preferred embodiments and modifications thereof, it should be understood by those skilled in the art that the foregoing and other modifications are exemplary only, and that equivalent changes in composition and detail may be employed therein without departing from the spirit and scope of the invention as claimed except as precluded by the prior art.

The embodiments of the invention in which an exclusive property or privilege is claimed are defined as follows:

1. A process for fractionating fast-pyrolysis oils from biomass materials to produce phenolic compounds/neutral fractions extract, wherein the neutral fractions have molecular weights of 100 to 800; said extract being substitutable for a part of the phenol in phenol-formaldehyde resins, said process comprising:

admixing said oils with an organic solvent having a solubility parameter of approximately 8.4–9.1 polar components in the 1.8–3.0 range and hydrogen bonding components in the 2–4.8 range;

separating the organic solvent-soluble fraction containing the phenolic compounds/neutral fractions from said mixture and admixing it with water to extract water-soluble materials therefrom;

separating the organic solvent-soluble fraction from said water fraction and admixing said solvent fraction with an aqueous alkali metal bicarbonate solution to extract strong organic acids and highly polar compounds from said solvent fractions; and separating the residual organic solvent-soluble fraction and removing the organic solvent therefrom to produce said phenolic compounds/neutral fractions extract.

2. The process of claim 1, wherein said organic solvent also exhibits low mutual solubility with water.

3. The process as claimed in claim 1, wherein said organic solvent is selected from the group consisting of acetate and propionate esters, methyl alkyl ketones and ethyl alkyl ketones.

4. The process as claimed in claim 3, wherein said organic solvent is selected from the group consisting of ethyl acetate, butyl acetate and methylisobutylketone.

5. The process as claimed in claim 4, wherein said organic solvent comprises ethyl acetate.

6. The process as claimed in claim 5, wherein the extraction utilizing ethyl acetate solvent is performed at a pH of approximately 2–4.

7. The process as claimed in claim 1, wherein said aqueous alkali metal bicarbonate solution is selected from the group consisting of sodium bicarbonate, potassium bicarbonate, ammonium bicarbonate and lithium bicarbonate.

8. The process as claimed in claim 7, wherein said bicarbonate solution comprises sodium bicarbonate.

9. The process as claimed in claim 8, wherein the extraction utilizing said sodium bicarbonate solution is carried out at pH of about 8.0–9.5.

10. The process as claimed in claim 1, wherein said oils are admixed with said organic solvent in an oil:solvent ratio of about 0.5:1 to 1:3 by weight.

11. The process as claimed in claim 1, wherein the organic solvent fraction is admixed with water at a water:solvent ratio of approximately 1:6 to 1:1 by weight.

12. The process as claimed in claim 1, wherein said organic solvent fraction is admixed with said carbonate solution at a bicarbonate solution:solvent ratio of about 6:1 to 0.5:1 by weight.

13. The process as claimed in claim 1, wherein said organic solvent is removed from the residual organic solvent fraction by evaporation to provide a dry phenol-containing composition.

14. The process as claimed in claim 1, wherein said fast-pyrolysis oils are produced from lignocellulosic materials.

15. The process as claimed in claim 14, wherein said lignocellulosic materials are selected from the group consisting of softwoods, hardwoods, pine sawdust, bark, grasses and agricultural residues.

16. The process as claimed in claim 1, wherein said phenolic compounds/neutrals fraction extract is capable of substituting for at least approximately up to 50% of the phenol in phenol-formaldehyde resins.

17. The process as claimed in claim 1, wherein said phenolic compounds/neutrals fraction extract include a high phenolic hydroxyl and aldehyde content.

18. The process as claimed in claim 1, wherein said organic solvent is evaporated from the residual organic solvent fraction, and said phenolic compounds/neutrals fraction extract is dried to form the basis for resins for molding compounds, plywood, and particle board.

19. The process as claimed in claim 1, wherein the portion of said organic solvent/oil mixture not extracted into the organic solvent-soluble fraction is further processed utilizing zeolite catalysts to form gasoline.

20. The process as claimed in claim 1, wherein said process is a batch process.

21. The process as claimed in claim 1, wherein said process is carried out on a continuous basis by performing said organic solvent and water extractions simultaneously while performing said alkali metal bicarbonate extraction in a countercurrent mode.

22. A process for producing a combined phenolic compounds/neutrals fraction extract from fast-pyrolysis of lignocellulosic materials comprising:
separating raw fast-pyrolysis oils into a carbohydrate-derived aqueous fraction and a phenolic-rich ethyl acetate soluble fraction by admixing an ethyl acetate solvent with said oils to extract the ethyl acetate-insoluble fraction;
separating the ethyl acetate-soluble fraction and washing it with water to further extract-soluble carbohydrates and derived polar compounds;
separating the ethyl acetate-soluble fraction and washing it with an alkali metal bicarbonate solution to extract the ethyl acetate-soluble strong organic acids and highly polar compounds from said ethyl acetate fraction; and
separating said ethyl acetate fraction containing phenolic compounds/neutrals fraction, and evaporating the ethyl acetate solvent to produce a combined phenolic compounds/neutrals extract.

23. The process as claimed in claim 22, wherein said phenolic and neutral fraction composition is suitable for use as a phenol substitute for up to at least approximately 50% of the phenol composition of phenolformaldehyde resins.

24. The process as claimed in claim 22, wherein said alkali metal bicarbonate solution is selected from the group consisting of sodium bicarbonate, potassium bicarbonate, ammonium bicarbonate and lithium bicarbonate.

25. The process as claimed in claim 24, wherein said aqueous metal bicarbonate solution comprises a sodium bicarbonate solution at a pH of about 8–9.5.

26. The process as claimed in claim 22, wherein said lignocellulosic materials are selected from the group consisting of softwoods, hardwoods, pine sawdust, bark, grasses and agricultural residues.

27. The process as claimed in claim 22, wherein said ethyl acetate solvent and said water are admixed with said oil simultaneously, and said alkali metal bicarbonate solution is subsequently flowed countercurrent to the ethyl acetate-soluble fraction to extract the soluble strong organic acids therefrom.

28. The process as claimed in claim 22, wherein said ethyl acetate/oils solution has a pH of about 2–4.

29. A process for fractionation of components of fast-pyrolysis oils comprising adding an ethyl acetate solvent to the oils to extract phenolic compounds/neutrals fraction into an ethyl acetate-soluble fraction, washing the ethyl acetate-soluble fraction first with water to extract water-soluble carbohydrates and polar compounds therefrom, extracting the ethyl acetate-soluble strong organic acids and highly polar compounds with a sodium bicarbonate solution, separating the ethyl acetate-soluble fraction containing a phenolic compounds/aromatic neutrals fraction, and evaporating the ethyl acetate solvent to produce a combined phenolic compounds/neutrals fraction composition.

30. The improvement of claim 29, wherein said combined phenolic compounds/neutrals composition is further treated with a sodium hydroxide solution to extract the phenolic compounds fraction from the neutrals fraction of said composition.

31. The improvement of claim 29, wherein said ethyl acetate/oils solution is at a pH of about 2–4, and said sodium bicarbonate solution/ethyl acetate-soluble fraction is at a pH of about 8–9.5.

* * * * *